(12) United States Patent
Zhang

(10) Patent No.: US 9,828,581 B2
(45) Date of Patent: Nov. 28, 2017

(54) EFFICIENT BOTTOM-IMPROVING BACILLUS AND COMPOUND BOTTOM-IMPROVING MICROBIAL AGENT PREPARED FROM THE SAME AND APPLICATIONS THEREOF

(71) Applicant: Jiangnan University, Wuxi (CN)

(72) Inventor: Liang Zhang, Wuxi (CN)

(73) Assignee: JIANGNAN UNIVERSITY, Wuxi, Chaina ( * ) Notice: Subject to any disclaimer, the term of this patent is extended or adjusted under 35 U.S.C. 154(b) by 0 days.

(21) Appl. No.: 15/113,441

(22) PCT Filed: Apr. 26, 2015

(86) PCT No.: PCT/CN2015/077473
§ 371 (c)(1),
(2) Date: Jul. 22, 2016

(87) PCT Pub. No.: WO2015/184935
PCT Pub. Date: Dec. 10, 2015

(65) Prior Publication Data
US 2017/0002310 A1    Jan. 5, 2017

(30) Foreign Application Priority Data

Jun. 3, 2014 (CN) .......................... 2014 1 0241782

(51) Int. Cl.
| | |
|---|---|
| *C12N 1/20* | (2006.01) |
| *C12R 1/07* | (2006.01) |
| *C02F 3/34* | (2006.01) |
| *C12R 1/125* | (2006.01) |
| *C12R 1/10* | (2006.01) |
| *C12R 1/11* | (2006.01) |
| *C02F 103/00* | (2006.01) |

(52) U.S. Cl.
CPC .................. *C12N 1/20* (2013.01); *C02F 3/34* (2013.01); *C02F 3/341* (2013.01); *C12R 1/07* (2013.01); *C02F 2103/005* (2013.01); *C02F 2103/007* (2013.01); *C02F 2303/20* (2013.01); *C12R 1/10* (2013.01); *C12R 1/11* (2013.01); *C12R 1/125* (2013.01)

(58) Field of Classification Search
CPC ....................................... C02F 3/341
See application file for complete search history.

(56) References Cited

FOREIGN PATENT DOCUMENTS

| CN | 103031253 A | 4/2013 |
| CN | 104017757 A | 9/2014 |
| KR | 1273444 B1 | 6/2013 |

*Primary Examiner* — Bin Shen
(74) *Attorney, Agent, or Firm* — Gokalp Bayramoglu

(57) ABSTRACT

The applicant provides a strain of *Bacillus tequilensis* ZSGD5, with accession number of the deposit of CCTCC NO.: M 2014004, deposited at the China Center for Type Culture Collection, Wuhan University, Wuhan City, China on Jan. 6, 2014. The applicant also provides a compound microecological *Bacillus* agent. The compound microbial agent comprises the following bacterial species: *Bacillus tequilensis*, Type I *Bacillus subtilis*, Type II *Bacillus subtilis*, Type I *Bacillus licheniformis*, Type II *Bacillus licheniformis*, *Bacillus pumilus*, and *Bacillus megaterium*. The *Bacillus tequilensis* provided in the present invention has an efficient water bottom cleaning capability, and can rapidly decompose and decrease the sludge at the bottom of a pond and effectively improve environmental waters for such phenomena as black water, and turbid water, so the *Bacillus tequilensis* can be used for water environment treatment in aquaculture and for urban wastewater treatment.

5 Claims, No Drawings

EFFICIENT BOTTOM-IMPROVING BACILLUS AND COMPOUND BOTTOM-IMPROVING MICROBIAL AGENT PREPARED FROM THE SAME AND APPLICATIONS THEREOF

TECHNICAL FIELD

The present invention relates to the field of industrial biological technologies, in particular to *Bacillus tequilensis*, and the application of a compound microbial agent prepared from the *Bacillus tequilensis* in aquaculture and wastewater treatment.

BACKGROUND

Using microecological agent to conduct water treatment or improvement and to maintain good ecological environment is a model of effective combination of modern biological engineering technologies with practical applications. However, owing to a large difference of functionality among various microorganisms, how to use the most effective and least microorganisms to achieve an excellent treatment effect is the direction of constant research and development for various scientific research institutions, universities and enterprises.

The residual baits and the excrement of cultured objects in current aquaculture seriously affect the culture environment, and rivers in or through many cities are enriched with organic matters due to discharge of wastewater with human living garbage, causing such phenomena as river water blackening. Developing effective microorganism population combinations based on the properties of microorganisms with different functions to treat surplus organic matters in culture waters and urban rivers has a quite active significance for future water improvement and treatment.

Aiming at the above problems in the prior art, the applicant provides an efficient bottom-improving *bacillus*, and a compound bottom-improving microbial agent prepared from the same and applications thereof. The *Bacillus tequilensis* provided in the present invention has an efficient water bottom cleaning capability, and can rapidly decompose and decrease the sludge at the bottom of a pond and effectively improve environmental waters for such phenomena as black water and turbid water, so the *Bacillus tequilensis* can be used for water environment treatment in aquaculture and for urban wastewater treatment.

SOLUTION

Summary of the Invention

The technical solution of the present invention is as follows:

The applicant provides a strain of *Bacillus tequilensis* (*Bacillus tequilensis*) ZSGD5, with accession number of the deposit number of CCTCC NO.: M 2014004. On Jan. 6, 2014, the strain was deposited at the China Center for Type Culture Collection, Wuhan University, Wuhan City, China.

The applicant provides a compound microecological *Bacillus* agent, which is a compound microbial agent comprising the following bacterial species:

*Bacillus tequilensis*, Type I *Bacillus subtilis*, Type II *Bacillus subtilis*, Type I *Bacillus licheniformis*, Type II *Bacillus licheniformis*, *Bacillus pumilus*, *Bacillus megaterium*;

The *Bacillus tequilensis*, Type I *Bacillus subtilis*, and Type I *Bacillus licheniformis*, respectively numbered as CCTCC NO: M 2014004, CCCTC NO: M 2011443, and CCTCC NO: M 2012458, are deposited at the China Center for Type Culture Collection, and the other bacterial species are commercially available. Type I *Bacillus subtilis* is deposited at the China Center for Type Culture Collection, Wuhan University, Wuhan City, China on Dec. 4, 2011 with the deposit number of CCCTC M 2011443. Type I *Bacillus licheniformis* is deposited at the China Center for Type Culture Collection, Wuhan University, Wuhan City, China on Nov. 14, 2012 with the deposit number of CCCTC M 2012458.

The compound microecological *Bacillus* agent has an effective viable count of $5.0 \times 10^8$-$2.0 \times 10^{10}$ cfu/g, with a dosage of 20-100 g/mu, and the bacterial species composition is as follows:

Bacterial species Viable count of bacterial species per gram of product, in cfu/g

*Bacillus tequilensis* $1.0 \times 10^8$-$5.0 \times 10^9$
Type I *Bacillus subtilis* $1.0 \times 10^8$-$5.0 \times 10^9$
Type II *Bacillus subtilis* $1.0 \times 10^8$-$5.0 \times 10^9$
Type I *Bacillus licheniformis* $5.0 \times 10^7$-$1.0 \times 10^9$
Type II *Bacillus licheniformis* $0.8 \times 10^7$-$5.0 \times 10^8$
*Bacillus pumilus* $0.2 \times 10^7$-$1.0 \times 10^8$
*Bacillus megaterium* $5.0 \times 10^7$-$1.0 \times 10^9$
Total viable count $5.0 \times 10^8$-$2.0 \times 10^{10}$.

The applicant provides an application of the compound microecological *Bacillus* agent, in the improvement on the quality of water at the bottom of a pond for aquaculture objects. The agent can effectively control the pollution caused by the bait residue and the excrement of cultured objects in the culture water, to maintain the increase in dissolved oxygen, suppress the moss at the bottom of a pond and reduce the contents of ammonia nitrogen, nitrite and hydrogen sulfide.

The applicant provides an application of the compound microecological *Bacillus* agent, in treatment of black water and turbid water in urban rivers. The agent can improve the rivers in the dead black water state and reduce the COD (Chemical Oxygen Demand) in water in rivers to 40%.

The main biological characteristics of *Bacillus tequilensis* are as follows: it is a gram positive bacterium, bacilliform, sized 0.7-0.8 um×2-3 um, free of capsule, having flagella, and movable.

The strain of *Bacillus tequilensis* comes from the bottom sludge in an aquaculture pond. A screening method is as follows: Bottom sludge taken from an aquaculture pond is added with sterile physiological saline. The mixture is oscillated on a shaking table at a temperature of 37° C. and at a speed of 120 rpm for 20 min. The supernatant is pipetted and added into liquid with the bottom sludge from other polluted river as matrix. The mixed solution is oscillated for 6 hr. After diluted by a factor of 10,000, the enriched liquid is applied to a solid plate with the bottom sludge from the polluted river as the unique matrix using a coating bar. The solid plate is cultured in a thermostatic incubator at 37° C. for 40-48 hr to obtain strains growing on the plate. After enlarged culture, the strains are screend.

The method for culturing the *Bacillus tequilensis* strains is as follows:

(1) Formulation of seed culture medium: 10 g/L peptone, 10 g/L sodium chloride and 5 g/L yeast powder are dissolved in the distilled water; after full dissolution, the pH is adjusted to 7.5-7.6; for solid culture medium, 15 g/L agar powder is added into the culture medium after pH is adjusted; the above prepared solution is sterilized at a temperature of 121° C. for 20 min.

(2) One loop of *Bacillus* is picked from the plate, transferred into the solid bevel culture medium in a sterilized test tube, and then cultured at a temperature of 37° C. for 18-24 hr.

(3) The above grown strain bevel is processed in a water bath at a temperature of 95-100° C. for 5-10 min, taken out, and rapidly cooled down to room temperature; 1 loop is picked and inoculated into a 500 mL conical flask with 50 mL of liquid culture medium, and then cultured on a shaking table at a temperature of 37° C. and a speed of 150 rpm for 18-24 hr; and then a bacterial solution with a viable count of $1\times10^7$-$3\times10^{10}$/mL is obtained.

(4) This strain can grow well in culture medium with nitrate or nitrite as a single nitrogen source, and the single nitrified culture medium includes: 20 g/L glucose, 2 g/L sodium nitrate (or 2 g/L sodium nirite), 2 g/L potassium dihydrogen phosphate, and 0.5 g/L magnesium sulfate, with a pH of 6.0-6.2.

The enlarged culturing method for *Bacillus tequilensis* strains is as follows:

Formulation of enlarged culture medium: 20 g/L glucose, 10 g/L yeast powder, 15 g/L peptone, 5 g/L potassium dihydrogen phosphate, and 1 g/L magnesium sulfate, with a pH of 7.0. The enlarged culture method is as follows: Liquid fermentation is conducted in a liquid fermentation tank; the following are maintained in the process: ventilation of 1:2 vvm, a stirring speed of 200 rpm and a pressure of 1 kg/m2; and the pH is controlled to be 6.0 using NaOH or HCl solution.

After the culture proceeds under the above conditions for 24-48 hr, spore bodies of bacterial species can be obtained, with spores accounting for over 95% of the total viable account, and a total spore account reaching $1\times10^9$-$5\times10^{10}$ cfu/mL in the fermented liquid. The bacterial bodies are collected from the fermented liquid through such means as centrifuging, and plate and flame filtration, and then spray dried, to obtain required spores. The obtained spore body bacterial species is used as a bacterial species raw material for preparing the compound bottom-improving microbial agent in the present invention.

The beneficial technical effects of the prevent invention are as follows:

After subjected to high-temperature granulation, the compound microecological agent prepared in the present invention can still maintain the high efficiency of the internally added bacterial species. In the tests in different culture waters and in waters from urban rivers, the compound microecological agent exhibits good functionality, and high viability of internally added microbial agents.

The bacterial species in the microecological agent prepared in the present invention can rapidly decompose the organic matters (baits, and excrement, etc., in culture water) in the bottom of the processed object water and thoroughly transform the organic matters to eliminate the offensive odor in the bottom; the bacterial species can prevent the pond's bottom from blackening and stinking; the bacterial species can control such toxic and hazardous substances as oxygen sulfide, and ammonia nitrogen, in the pond; and the bacterial species can prevent yellow slurry water, black water, red water, thick water, and turbid water from occurring, thus to have evident inhibiting effect on the growth of hazardous algae, including moss, and blue-green algae, so that the object water is maintained in good ecological environment.

DETAILED DESCRIPTION OF THE INVENTION

Embodiment

1. Screening of Efficient Bottom-Improving Bacterial Species

The microbial strain suitable for water quality improvement is separated from the bottom slurry and water in an aquaculture pond, and the genus of the bacterial species is effectively and accurately determined through such means for the strain as morphological observation, physiological & biochemical experiments, and 16S rDNA analysis.

2 g of bottom slurry sample taken from a crab culture pond in Jiangyan, Taizhou, Jiangsu is weighed. 98 mL of sterile physiological saline is added. The mixture is oscillated on a shaking table at a temperature of 37° C. and at a speed of 120 rpm for 20 min. 1 mL of supernatant is pipetted into the liquid with the bottom slurry taken from a polluted river in Wuxi City as matrix. The obtained liquid is oscillated for 6 hr. After the enriched liquid is diluted by a factor of 10,000, an applying rod is used to apply the diluted liquid onto a solid plate with the bottom sludge taken from the river as a unique matrix, and the solid plate is cultured in a thermostatic incubator at a temperature of 37° C. for 40-48 hr. Then, three strains growing on the plate are obtained, which are numbered as ZSGD-1, ZSGD-5, and ZSGD-9, respectively. Single colonies are picked for enlarged culturing. The bacterial bodies obtained from the enlarged culturing are used for the processing test of the polluted river water. A strain with a relatively good effect, that is, ZSGD-5, is picked out. The identification and test results of 16S rDNA and physiological & biochemical properties show that this bacterial species belongs to *Bacillus tequilensis*, and this *Bacillus* can grow rapidly at a low oxygen concentration and consume the nutrients in polluted waters.

n-1 classification and naming is *Bacillus tequilensis*, deposited at the China Center for Type Culture Collection on Jan. 6, 2014, and with accession number of the deposit of CCTCC M 2014004.

2. Enlarged Culture of Strain and Collection of Product

According to the above-mentioned culture and enlarged culture methods for the strain, the enlarged culture of bevel *Bacillus tequilensis* CCTCC M 2014004 is carried out to obtain the spore solution of *Bacillus subtilis* with a certain concentration; the spore solution is centrifuged, spray-dried, etc. to obtain spore powder product.

3. Preparation Method for the Compound Bottom-Improving Microbial Agent (Namely, Compound Microecological *Bacillus* Agent)

The screened *Bacillus tequilensis* and other effective strains are mixed according to the viable count ratio in respective solid bacterial powder; the viable bacteria adding ratios (based on ratio to total viable count of product) of the solid bacterial powder of various effective strains are as follows:

Bacterial species Viable count of bacterial species per gram of product, in cfu/g

*Bacillus tequilensis* (CCCTC M 2014004) $1.0\times10^9$
Type I *Bacillus subtilis* (CCCTCM 2011443) $1.0\times10^9$
Type II *Bacillus subtilis* $1.0\times10^9$
Type I *Bacillus licheniformis* (CCTCC M 2012458) $1.0\times10^8$
Type II *Bacillus licheniformis* $1.0\times10^8$
*Bacillus pumilus* $0.2\times10^8$
*Bacillus megaterium* $1.0\times10^8$
Total viable count $5.0\times10^9$ All bacterial species numbered above are deposited at the China Center for Type Culture Collection, whereas all of Type II *Bacillus subtilis*, Type II *Bacillus licheniformis*, *Bacillus pumilus*, and *Bacillus megaterium* are provided by Taizhou LvShengYuan Biological Co., Ltd.

After the above various kinds of bacterial powder are evenly mixed at predetermined ratios, one or more carriers (bran powder, glucose, corn powder, rice bran powder, zeolite powder, diatomite, activated carbon, sericite powder) are added to supplement the total weight to 100% (with *Bacillus* as effective component. Carriers are added so that the total weight of product conforms to that the final viable count reaches $5.0\times10^9$ cfu/g). Granulation is carried out to get microbial agent granules, and then the microbial agent granules are put into use.

Each kind of effective single bacterial powder is prepared strictly according to the above method, and then, the compound bottom-improving microbial agent described in the present invention, also called compound microecological Bacillus agent, can be obtained. This product is used to conduct effective bottom improvement on waters polluted by various organic matters so that the bottom slurry turns from black to yellow, and can reduce residual baits and excrement in the bottom of a culture water pond, and effectively eliminate such substances as ammonia nitrogen, nitrite, and hydrogen sulfide at the bottom of a pond.

In the above whole processing process, it shall be ensured that the environment is clean to avoid contamination. The environmental humidity is controlled to be below 70%, and the moisture content in each raw material to be below 15%. This product prepared can be stored for 18 months at normal temperature; the shelf life can reach 36 months at a temperature of −18° C. and the viable count is stable within the shelf life.

4. Test Example 1: The Compound Microecological *Bacillus* Agent was Used for Improvement of *Carassius auratus* Culture Water.

Taking water sample: The water sample was taken at a position 30 cm below water surface and 1.5 m away from bank in a culture pond in Taicang, Suzhou. The water sample was processed according to the Specification for Marine Monitoring. In the test, the culture water temperature was 22-27° C., and the result in the control pond was obtained without using the compound bottom-improving microbial agent.

The microbial agent granules were spread into the pond at a dose of 500 g per mu·m.

The processing results are shown in Table 1.

TABLE 1

| | Ammonia nitrogen (ppm) | | Nitrite (ppm) | | Total inorganic nitrogen (ppm) | | Dissolved oxygen (ppm) | | Phosphate (ppm) | |
|---|---|---|---|---|---|---|---|---|---|---|
| | Control pond | Test pond | Control pond | Test pond | Control pond | Test pond | Control pond | Test pond | Control pond | Test pond |
| Before processing | 2.4 | 2.5 | 0.15 | 0.14 | 0.249 | 0.241 | 3.2 | 3.1 | 0.065 | 0.067 |
| 2 days after processing | 2.3 | 1.9 | 0.13 | 0.09 | 0.252 | 0.185 | 3.1 | 3.5 | 0.093 | 0.043 |
| 3 days after processing | 2.3 | 0.08 | 0.16 | 0.07 | 0.247 | 0.102 | 3.4 | 4.5 | 0.087 | 0.038 |
| 4 days after processing | 2.4 | 0.07 | 0.15 | 0.06 | 0.253 | 0.103 | 3.6 | 5.2 | 0.087 | 0.029 |

According to the data in table 1, it can be seen that, the compound microbial agent can effectively decrease the ammonia nitrogen, nitrite, total inorganic nitrogen, and phosphate in water and can increase the content of dissolved oxygen in water.

5. Test Example 2: The Compound Microecological *Bacillus* Agent was Used for Treatment of Black Water in River.

Two polluted water samples were taken at different positions of a polluted river in Wuxi. Treatment tests were conducted with this microbial agent respectively; the control group was not processed. The test scale was 5 L, and COD as tested according to the corresponding China national standard. The microbial agent granules were added at a dose of 500 g per mu·m. The processing results are shown in Table 2.

TABLE 2

| | Ammonia nitrogen (ppm) | | Nitrite (ppm) | | Total inorganic nitrogen (ppm) | | Dissolved oxygen (ppm) | | Phosphate (ppm) | |
|---|---|---|---|---|---|---|---|---|---|---|
| | Control pond | Test pond | Control pond | Test pond | Control pond | Test pond | Control pond | Test pond | Control pond | Test pond |
| Before processing | 2.4 | 2.5 | 0.15 | 0.14 | 0.249 | 0.241 | 3.2 | 3.1 | 0.065 | 0.067 |
| 2 days after processing | 2.3 | 1.9 | 0.13 | 0.09 | 0.252 | 0.185 | 3.1 | 3.5 | 0.093 | 0.043 |
| 3 days after processing | 2.3 | 0.08 | 0.16 | 0.07 | 0.247 | 0.102 | 3.4 | 4.5 | 0.087 | 0.038 |
| 4 days after processing | 2.4 | 0.07 | 0.15 | 0.06 | 0.253 | 0.103 | 3.6 | 5.2 | 0.087 | 0.029 |

According to the data in table 2, it can be seen that, when this microbial agent is used to process the polluted water in river, it can effectively decrease the COD in the polluted water in the river.

The invention claimed is:

1. A compound microecological *Bacillus* agent, wherein the compound microbial agent comprises the following bacterial species:

Bacillus tequilensis, Type I Bacillus subtilis, Type II Bacillus subtilis, Type I Bacillus licheniformis, Type II Bacillus licheniformis, Bacillus pumilus, Bacillus megaterium;

the *Bacillus tequilensis*, Type I *Bacillus subtilis*, and Type I *Bacillus licheniformis*, respectively numbered as CCTCC NO.: M 2014004, CCCTC NO.: M 2011443, and CCTCC NO.: M 2012458, are deposited at the China Center for Type Culture Collection, and all of other bacterial species are commercially available.

2. The compound microecological *Bacillus* agent according to claim 1, wherein the effective viable count of the compound microecological *Bacillus* agent is $5.0 \times 10^8$-$2.0 \times 10^{10}$ cfu/g, the dosage is 20-100 g/mu, and the bacterial species composition is as follows:

Bacterial species viable count of bacterial species per gram of product, in cfu/g
Bacillus tequilensis $1.0 \times 10^8$-$5.0 \times 10^9$
Type I Bacillus subtilis $1.0 \times 10^8$-$5.0 \times 10^9$
Type II Bacillus subtilis $1.0 \times 10^8$-$5.0 \times 10^9$
Type I Bacillus licheniformis $5.0 \times 10^7$-$1.0 \times 10^9$
Type II Bacillus licheniformis $0.8 \times 10^7$-$5.0 \times 10^8$
Bacillus pumilus $0.2 \times 10^7$-$1.0 \times 10^8$
Bacillus megaterium $5.0 \times 10^7$-$1.0 \times 10^9$
Total viable count $5.0 \times 10^8$-$2.0 \times 10^{10}$.

3. The compound microecological *Bacillus* agent according to claim 1, wherein the compound microecological *Bacillus* agent is used for improving the quality of the bottom water in a pond for aquaculture.

4. The compound microecological *Bacillus* agent according to claim 1, wherein the compound microecological *Bacillus* agent is used for treatment of black water and turbid water in urban rivers.

5. The compound microecological *Bacillus* agent according to claim 4, wherein the compound microecological *Bacillus* agent improve the status of dead black water in rivers and decrease the Chemical Oxygen Demand (COD) in water rivers to 40%.

* * * * *